United States Patent
Krzysik

(10) Patent No.: US 11,633,347 B2
(45) Date of Patent: Apr. 25, 2023

(54) HYDROUS HAIR CARE COMPOSITIONS AND METHODS

(71) Applicant: Innospec Limited, Cheshire (GB)

(72) Inventor: Duane Krzysik, Salisbury, NC (US)

(73) Assignee: Innospec, Ltd., Ellesmere Port (GB)

( * ) Notice: Subject to any disclaimer, the term of this patent is extended or adjusted under 35 U.S.C. 154(b) by 131 days.

(21) Appl. No.: 16/644,864

(22) PCT Filed: Aug. 24, 2018

(86) PCT No.: PCT/US2018/047875
§ 371 (c)(1),
(2) Date: Mar. 5, 2020

(87) PCT Pub. No.: WO2019/060088
PCT Pub. Date: Mar. 28, 2019

(65) Prior Publication Data
US 2020/0253856 A1    Aug. 13, 2020

Related U.S. Application Data

(60) Provisional application No. 62/562,653, filed on Sep. 25, 2017.

(51) Int. Cl.
| | |
|---|---|
| A61Q 5/00 | (2006.01) |
| A61Q 5/12 | (2006.01) |
| A61K 8/898 | (2006.01) |
| A61K 8/06 | (2006.01) |
| A61K 8/86 | (2006.01) |
| C08G 77/26 | (2006.01) |
| C08G 77/388 | (2006.01) |
| C08L 83/08 | (2006.01) |

(52) U.S. Cl.
CPC ............... *A61K 8/898* (2013.01); *A61K 8/06* (2013.01); *A61K 8/86* (2013.01); *A61Q 5/12* (2013.01); *C08G 77/26* (2013.01); *C08G 77/388* (2013.01); *C08L 83/08* (2013.01)

(58) Field of Classification Search
None
See application file for complete search history.

(56) References Cited

U.S. PATENT DOCUMENTS

| | | |
|---|---|---|
| 6,605,577 B1 | 8/2003 | Harrison et al. |
| 6,709,648 B2 | 3/2004 | Sako et al. |
| 8,097,602 B1 | 1/2012 | Holzer |
| 2003/0134760 A1 | 7/2003 | Harrison et al. |
| 2006/0057217 A1 | 3/2006 | Utschig et al. |
| 2009/0110703 A1* | 4/2009 | Tolla .............. A61Q 3/00 424/59 |
| 2011/0110991 A1 | 5/2011 | Garrison et al. |
| 2011/0110992 A1 | 5/2011 | Garrison et al. |
| 2012/0021025 A1 | 1/2012 | Bendejacq et al. |
| 2013/0034515 A1 | 2/2013 | Stone et al. |
| 2014/0308227 A1 | 10/2014 | Mabille |
| 2016/0228342 A1* | 8/2016 | Rose .............. A61Q 5/12 |
| 2016/0271023 A1 | 9/2016 | Bekemeier et al. |
| 2016/0310404 A1 | 10/2016 | Schrott et al. |
| 2017/0189313 A1 | 7/2017 | Tan et al. |

FOREIGN PATENT DOCUMENTS

| | | |
|---|---|---|
| JP | 2011-105631 A | 6/2011 |
| JP | 2012-092040 A | 5/2012 |
| WO | 2016164292 A1 | 10/2016 |

OTHER PUBLICATIONS

International Search Report application No. PCT/US18/47875, dated Nov. 26, 2018.
International Search Report application No. PCT/US18/47911, dated Nov. 7, 2018.
"One Week Straightener", ID 573472, Database GNPD (Online), Mintel, Aug. 2006.
"Straight Away Conditioner", ID 2452005, Database GNPD (Online), Mintel, Jun. 2014.
"Anti-Frizz Serum", ID 707129, Database GNPD (Online), Mintel, May 2007.
"Innospec—Inner Beauty—Product Guide." Feb. 28, 2017. https://customchemicalservices.com/wp-content/uploads/2017/02/INN15006_Product_Guide_FINAL.pdf.
Product Information—Microsil® Finish. Nov. 30, 2015. https://www.asharrison.com.au/wp-content/uploads/2015/11/Microsil®-Finish.pdf.
Office Action dated Jul. 26, 2022 in related Japanese Patent Application No. 2020-517159.
Office Action dated Aug. 9, 2022 in related Japanese Patent Application No. 2020-517191.
Written Opinion dated Jul. 24, 2022 in related Singapore Patent Application No. 11202002414S.
Written Opinion dated Jul. 24, 2022 in related Singapore Patent Application No. 1120200237711.
Office Action dated Jul. 5, 2022 in related Chinese Patent Application No. 201880062383.1.

* cited by examiner

*Primary Examiner* — Jyothsna A Venkat
(74) *Attorney, Agent, or Firm* — Carlos A. Fisher; Stout, Uxa & Buyan, LLP

(57) ABSTRACT

Methods and compositions for preventing or reducing hair frizz. The compositions are preferably oil-in-water or water-in-oil emulsions comprise at least one polysiloxane fluid component selected from an amodimethicone and a polysiloxane component comprising a plurality of hindered amine side chains. The compositions also comprise a silicone-compatible, volatile or non-volatile liquid carrier component, preferably comprising a component selected from a low molecular weight, volatile siloxy component; a hydrocarbon; and an alcohol. The compositions are preferably combing cremes, sprays or mousses, and are suitable for use a "leave-in" hair care product, or as a touch-up hair care product suitable for use during the day.

9 Claims, 3 Drawing Sheets

HYDROUS HAIR CARE COMPOSITIONS AND METHODS

CROSS-REFERENCE TO RELATED PATENT APPLICATIONS

This application claims the benefit of U.S. provisional patent application Ser. No. 62/562,653, filed Aug. 25, 2017, which is hereby incorporated by reference herein in its entirety.

FIELD OF THE INVENTION

The present invention concerns water-containing compositions and methods for reducing and preventing frizzy hair. Such compositions may comprise and/or be comprised in hair care products including, without limitation, shampoos, conditioners, styling gels, creams, serums, sprays, and liquids, and restorative hair care products. Preferably, the compositions of the invention may be used primarily or substantially solely as an anti-frizz hair treatment, particularly, though not solely, as a composition to be left in the hair for an extended time (herein termed a "leave-in" or "leave-on" hair care product). In other examples the compositions of the invention may be a component of a multi-purpose hair care composition.

BACKGROUND

Hair fizz is a problem that commonly occurs in people who have wavy and curly hair, particularly when humidity levels and/or dew points are high; this typically occurs in the summer months and at tropical latitudes. However, relative humidity, the ratio of the partial pressure of water vapor to the equilibrium vapor pressure of water at a given temperature, depends on both temperature and the local air pressure, and high relative humidity can be attained at low temperatures with comparatively little water vapor. Thus, depending upon local air pressure, in some cases relative humidity greater than only about 50% can be considered sufficiently high humidity to cause hair frizz.

What is normally thought of as "hair" (i.e., the hair shaft, external to the hair root under the skin) is comprised of keratin, a protein in which disulfide bonds hold the strands together. The hair shaft comprises three layers: the medulla, the cortex and the cuticle. The medulla is a thin core of transparent cells and air spaces. The cortex forms the bulk of the hair shaft and usually contains pigment and long keratin filaments, which are held together by disulfide and hydrogen bonds.

The cuticle is a protective layer comprised of overlapping cells, organized like fish scales facing downwards. The outer cuticle holds the hair shaft in the hair follicle by means of a bond. When it is healthy, it also minimizes the movement of water (moisture) in and out of the underlying cortex. However, chemical processes and weathering can lift the cuticle from the cortex and disrupt this balance.

When high humidity causes frizz, the cuticle layer of hair is raised. The hair cuticles normally regulate the water absorption in the hair. Raised cuticles occur in the areas of naturally curly hair in which there is a bend in the curl and permit moisture to be absorbed by the hair cortex. As a result, the hair may appear dry (because the cuticle may indeed be dry); the hair shaft increases in volume due to the water uptake by the cortex causing the hair to swell. In general, extremely wavy and curly hair tends to have more frizz than straight hair because the hair does not properly regulate the amount of water absorbed by the hair.

In addition to curly or wavy hair, hair that has been damaged by chemical processing (such as straightening, permanent waving, hair dyeing or bleaching), heat (such as by blow drying and the use of flat irons or curling irons), mechanical damage (such as by excessive combing and brushing) and environmental damage (such as sunlight, air or water pollution, chlorine, etc.) causes cuticle damage, permitting water to enter the cortex and the hair to absorb more moisture.

Throughout history natural oils have been used to control fizz. Some common natural oils include almond, olive, coconut, moringa, avocado, shea butter, argan, sunflower oil, etc. Additionally, mineral oil and fats have been used. However, oils tend to make the hair look wet, leave the hair greasy and oily to the touch, and to transfer easily to bedding and clothes.

More recently, various conditioners and "leave-in" products have been formulated to control fizz, partially due to trends dissuading people with wavy and curly hair people from straightening their hair using flat irons and formaldehyde (often called the "Brazilian Blowout") and embracing their natural curl. Specialized products have entered this category and among them are leave-in water-based conditioning products. While such products have been primarily marketed to those of Latino and African heritage, in recent years they have become more popular in the general population of women with thick curly or wavy hair. Thicker hair that is very wavy to very curly is very susceptible to high humidity frizz. Such products generally fall into four categories:

a) Styling products, like gels, creams, hair mousse and hair spray to help keep the hair in place. However, organic styling resins such as these cause the hair to feel unnatural and stiff.

b) Water and alcohol-based products containing fatty quaternary ammonium components, fatty alcohols and natural or petroleum-based oils. These products may also contain some amounts of cyclomethicone and dimethicone.

c) Anhydrous alcohol-based serums and sprays containing cyclomethicones, dimethicones and alkyl modified silicones. In these products the volatile component (which may comprise ingredients such as ethanol and volatile silicones) help to dehydrate the hair cortex, and after evaporation of the volatile components a film of the non-volatile silicones and other components forms on the cuticle to seal the hair from moisture.

d) Anhydrous anti-frizz serums, spritzes and sprays. Such anhydrous serums may contain cyclomethicones, dimethicones and significant concentrations of high molecular weight and/or high viscosity silicones, such as dimethicone gum and dimethiconol gum. As in the alcohol-base serums and sprays, in these products the low molecular weight, volatile silicone helps to replace moisture from the hair, evaporates after application, and leaves a film of the high molecular weight non-volatile silicone on the hair to seal the hair from moisture. Typical serum formulations have a viscosity ranging from about 500 centipoise (cP) to about 5,000 cP, while spray products typically have a viscosity of less than 200 cP.

Song et al., US2016/0374932 and WO2015/200778 describe a composition comprising an amodimethicone/ morpholinomethyl silsesquioxane copolymer made by emulsion polymerization in water.

Uehara et al., WO2004/030646 discloses a composition comprising a mixture of high, medium, and low viscosity silicones; an amidoamine; an acid; a high melting point fatty compound and water.

Richards, WO2010/003793 discloses an aqueous composition comprising three kinds of silicones: an alkyl modified silicone, a second silicone comprising, for example, a polydimethylsiloxane gum, and a functionalized silicone such as an amino-functionalized silicone (e.g., an amodimethicone).

Scholz, US2002/0197227 discloses a hair care composition comprising: a high viscosity silicone polymer, a non-volatile carrier fluid and volatile silicone based carrier fluid.

Garrison et al, US2011/0110991 discloses a composition comprising a hydrophobic particulate material, a silicone-based hydrophobic film former and a volatile hydrocarbon or silicone fluid.

Singer et al., U.S. Pat. No. 8,591,872 discloses a composition comprising, in a cosmetically acceptable carrier, the following ingredients: at least one non-hydroxide base chosen from monoethanolamine, triethanolamine and ethylenediamine; one or more protein denaturants such as urea and/or hydroxyethylurea; an alkoxysilane; and optionally at least one fatty substance.

These products perform with varying degrees of efficacy, and many users of these products are not satisfied with the limited degree of frizz control that the above technologies provide. Therefore there is a need for high performance, water-based frizz control products particularly, but not exclusively, in "leave-in" formulations that are acceptable to the consumer. Such a formulation would ideally provide good application feel (without heaviness, stiffness, greasiness or a "watery" feel), a good ability to be smoothly distributed and spread on the hair and, when dry, such a formulation would ideally leave the hair manageable, and feeling and looking natural. Such products are generically known as combing creams, combing lotions and combing sprays.

It would be desirable that a combing cream, lotion and spray, and similar products, would increase the lubricity of the hair shaft without imparting excessive "heaviness" or an oily or pasty look to the hair. Increased lubricity causes the surface of the hair strands to slip in relation of each other, thereby helping detangle the hair, increasing the ability of curly or wavy hair to be combed easily, and helping protect the hair from mechanical damage from combing or brushing. Combing creams and lotions are usually dispensed to the hands from a jar, bottle, or tube, and combing sprays are sprayed on to the hair. Preferably, such a product/formulation is capable of being applied to wet hair (or as a touch up conditioner) in an effective amount, and combed through the hair to adequately coat the hair from root to the tip of each hair strand. Such a combing product would ideally be suitable to be left on the hair throughout the day.

SUMMARY OF THE INVENTION

The present invention is directed to water-containing compositions, such as combing creams, lotions, mousses, gels and sprays, for reducing or eliminating frizz from hair, such compositions having good application feel (a good ability to be smoothly distributed and spread on the hair and, when dry, to leave the hair manageable), and methods for making and using such compositions.

According to a first embodiment, there is provided a water-containing flowable composition comprising:

a) 3.0% or more by weight, of a polysiloxane fluid component containing an ingredient selected from the group consisting of:
  i) an amodimethicone component, and
  ii) a polysiloxane comprising a plurality of hindered amine side chains, and
b) water.

By "polysiloxane component" is meant a compound containing units of substituted and/or unsubstituted siloxane: one or more chain of alternating silicon atoms and oxygen atoms, frequently combined with carbon or hydrogen or both. Unless specifically indicated otherwise, the term "polysiloxane" is meant to include dimethiconols and other siloxanes having an end chain hydroxyl group.

In a second embodiment the present invention comprises an oil-in-water emulsion or water-in-oil emulsion which contains a) at least 3.0%, by weight, of a polysiloxane fluid component containing an ingredient selected from the group consisting of:
  i) an amodimethicone component, and
  ii) a polysiloxane component comprising a plurality of hindered amine side chains;
b) water, and
c) an optional silicone-compatible, volatile or non-volatile liquid carrier component.

By "silicone-compatible, volatile or non-volatile liquid carrier component" in this specification is meant either a silicone-compatible, volatile liquid carrier component or a silicone-compatible, non-volatile liquid carrier component.

By the terms "oil-in-water" or "water-in-oil" is meant a multiphasic system comprising immiscible water and oil phases. It will be understood that by "oil" is meant to include silicone-containing liquids.

Preferred embodiments of the present invention, for example as listed below, may contain a "silicone-compatible, volatile liquid carrier component", which comprises at least one volatile component, and which, unless specifically indicated otherwise, may also include a non-volatile component as well.

It will be understood that other embodiments of the invention contain a "silicone-compatible, non-volatile liquid carrier component", which comprises one or more non-volatile component and lacks any volatile component.

It will also be understood that, the scope of the present invention extends to include additional embodiments, otherwise identical to each embodiment contained herein listing a silicone-compatible, volatile liquid carrier component, in which the silicone-compatible liquid carrier component is a silicone compatible, non-volatile liquid carrier component.

In a third embodiment the present invention comprises a water-containing anti-frizz hair composition which contains a) at least 3.0%, by weight, of a polysiloxane fluid component containing an ingredient selected from the group consisting of:
  i) an amodimethicone component, and
  ii) a polysiloxane component comprising a plurality of hindered amine side chains;
b) water,
c) an optional silicone-compatible, volatile and or non-volatile liquid carrier component, and
d) an alkylsiloxysilicate, such as a trimethylsiloxysilicate.

According to a fourth embodiment, there is provided a water-containing anti-fizz hair composition comprising:

a) 3.0% or more, by weight, of a polysiloxane fluid component comprising an propoxytetramethyl piperidinyl dimethicone component b) water, and
c) an optional silicone-compatible, volatile liquid carrier component.

According to a fifth embodiment, there is provided a water-containing anti-frizz hair composition comprising:
a) 3.0% or more, by weight, of a polysiloxane fluid component comprising a trimethylsilylamodimethicone component and
b) an optional silicone-compatible, volatile liquid carrier component.

According to a sixth embodiment, there is provided a water-containing anti-frizz hair composition comprising:
a) 3.0% or more, by weight, of a polysiloxane fluid component comprising an aminopropyl siloxane component
b) water, and
c) an optional silicone-compatible, volatile liquid carrier component.

According to a seventh embodiment, there is provided a water-containing anti-frizz hair composition comprising:
a) 3.0% or more, by weight, of a polysiloxane fluid component comprising the structure

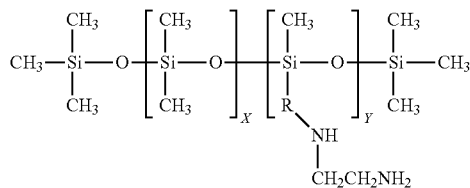

wherein X+Y is between about 50 to about 500 and R is a $C_3$ to $C_5$ alkylene group;
b) water, and
c) an optional silicone-compatible, volatile liquid carrier component.

According to an eighth embodiment there is provided a method of reducing or preventing hair frizz, comprising the steps:
a) applying to hair a composition of any of the first through seventh embodiments; and
b) distributing said composition along a plurality of hair shafts.

According to a ninth embodiment there is provided a method of increasing curl memory, comprising the steps:
I) applying to hair a composition of any of the first through seventh embodiments; and
II) distributing said composition along a plurality of hair shafts.

According to a tenth embodiment there is provided the use of a composition of any of the first through seventh embodiments to reduce hair frizz.

According to an eleventh embodiment there is provided the use of a composition of any of the first through seventh embodiments to reduce hair fizz by more than 70% when held at 80° F. and 80% humidity, as compared to substantially identical hair not treated with said composition, but otherwise handled identically.

According to a twelfth embodiment there is provided the use of a composition of any of the first through seventh embodiments to increase curl memory, as compared to substantially identical hair not treated with said composition but otherwise handled identically.

According to a thirteenth embodiment there is provided the method or use of any of the eighth through twelfth embodiments to reduce hair frizz.

The invention is not limited to the embodiments described above, and additional embodiments are disclosed in the disclosure of the specification.

The combination of amino-substituted polysiloxane fluid components as described herein at concentrations at or above 3.0% by weight, or at or above about 3.1% by weight, or at or above about 3.2% by weight, or at or above about 3.3% by weight, or at or above about 3.4% by weight, or at or above about 3.5% by weight, or at or above about 3.6% by weight, or at or above about 3.7% by weight, or at or above about 3.8% by weight, or at or above about 3.9% by weight, or at or above about 4.0% by weight, about 4.1% by weight, or at or above about 4.0% by weight, or at or above about 4.1% by weight, or at or above about 4.2% by weight, or at or above about 4.3% by weight, or at or above about 4.4% by weight, or at or above about 4.5% by weight, or at or above about 4.6% by weight, or at or above about 4.7% by weight, or at or above about 4.8% by weight, or at or above about 4.9% by weight, or at or above about 5.0% by weight, optionally with one or more silicone-compatible, non-aqueous volatile carriers has been found to solve the problem of providing a reduction in hair frizz (as determined greater that 50%, or greater than 60%, or greater than 70%, or greater than 80%, or greater than 85% as compared to identical and otherwise identically-treated hair not contacted with said composition.

The methods and compositions disclosed herein may be used on hair that has not been artificially colored (e.g., dyed, bleached, or pigmented), or on hair that has been artificially colored.

In some embodiments the invention is drawn to a use of a composition of the first through seventh embodiments to treat hair that has been artificially colored to retain its color, as compared to otherwise identical colored hair not treated with such a composition.

In some embodiments the invention is drawn to a use of a composition of the first through seventh embodiments to increase curl retention and/or curl memory properties of hair treated with the composition, as compared to identical and otherwise identically-treated hair not treated with said composition.

In a further embodiment, the water-containing compositions containing amino-substituted polysiloxanes at concentrations at or above 3.0% by weight, with one or more silicone-compatible, non-aqueous volatile carriers and a dimethicone or dimethiconol component with a viscosity of greater than 150,000 cSt (centiStokes) at a concentration of above 5% by weight and/or a trimethylsiloxy-silicate at above 5% by weight provide a significant reduction in hair frizz, as measured according to the procedures set forth under the heading High Humidity Frizz Control Test Method (see Examples section below) and additionally provide curl retention and curl memory properties (as measured according to the procedures set forth in e.g., Example 10, below) compared with untreated otherwise identical hair under the same test conditions.

Various suitable methods for determining frizz reduction are available in the art. A preferred method is detailed below under the heading High Humidity Frizz Control Test Method; see Examples section below.

As used herein, viscosity of a fluid may be expressed as centipoise (cP) or centistokes (cSt), wherein cSt=cP divided by the specific gravity (SG) of the fluid. Generally, the viscosity of components are expressed in cSt and the viscosity of formulations are expressed in cP. Where no temperature is referred to, viscosity is measured at 25° C.

As used herein, the expression "at least one" means one or more, and thus includes individual components as well as mixtures and/or combinations of components.

As used herein, the words "a" and "an" means one or more, and thus includes individual components as well as mixtures and/or combinations of components.

As used herein, the term "about" means plus or minus 10% of the indicated number.

As used herein, the term "hair" means keratinous fibers. As used, the term "hair" may include "living" hair, i.e. on a living body, or may be "non-living" i.e. in a wig, hairpiece or other aggregation of non-living fibers, such as those used in textiles and fabrics. Mammalian hair, e.g. human hair, is preferred in various embodiments. However, animal hair (such as dog or horse), wool, fur and other keratinous fibers are suitable for use in the methods and with the compositions described herein.

The term "hydrous" or "water-containing" as used herein is intended to mean that the composition contains greater than trace amounts of unbound water, such as, for example, about 1% or more by weight, or about 2.5% or more by weight, or about 5% or more by weight, based on the weight of the composition.

As used herein, the phrase "minimizing damage" to the hair and/or skin is intended to mean that the breakage of the hair has been reduced or eliminated and/or the skin is substantially not irritated by topical exposure to a referenced composition for 15 minutes, followed by rinsing with water.

As used herein, the term "ready-to-use composition" means a composition intended to be applied in unmodified form to the keratin fibers, i.e. it may be stored in unmodified form before use or may result from the extemporaneous pre-mixing of two or more compositions.

As used herein, the term "applying" a composition to the hair or "treating" the hair with a composition is intended to mean contacting and distributing a hair care composition on the hair.

As used herein, "cosmetically acceptable" means that the item in question is compatible with human or animal skin or hair.

As used herein, "cosmetically acceptable carrier" means a carrier that is compatible with human or animal skin or hair and feels pleasant with no adverse odor.

As used herein, "conditioning" means imparting to at least one keratinous fiber at least one property chosen from "combability" (the ability of wet or dry hair to be combed easily), manageability, shine, and softness.

As used herein, "curl definition" refers to curly hair tresses in which the individual hairs align with each other to a sufficient degree to render a discernible curl shape to the tress as a whole.

As used herein "curl memory" refers to curly hair tresses in which a curl snaps back into its original shape after the curl is stretched and released.

As used herein "curl fatigue" means that a curl having initial curl memory does not snap back into its original shape after the curl is stretched and released more than about three times.

As used herein "lack of curl fatigue" means that a curl having initial curl memory continues to snap back into its original shape after the curl is stretched and released more than about three times.

As used herein, "curl retention" means the ability of hair having a defined curl, or induced to have a defined curl, to have curl memory when the hair is treated with a composition as compared to untreated, otherwise identical hair.

As used herein, "silicone-compatible" means silicone-miscible.

As used herein, the term "frizz" or "frizzy" hair means that the hair contains short strands sticking up (for example where the hair is parted or elsewhere along the hair length) and projecting away from the main body of hair; this type of frizz is especially noticeable on people with straight hair who are trying to achieve a smooth style. Additionally, "frizz" may be used to refer to strands of wavy or curly hair that do not align with others to form a defined wave or curl.

As used herein the term "flowable" means non-solid, substantially fluid, and having the property of changing its shape at a relatively steady rate when acted upon by a force.

As used herein the term "permitted to dry", with respect to hair, means allowing volatile components applied to the hair to evaporate to the point that an ordinary person would consider the hair dry to the touch.

As used herein, the term "volatile" means that at least about 60% by weight of a component evaporates at temperature of about 40° C. at a pressure of about 100 kPa (1 bar) within a time period of about 100 minutes.

As used herein, the terms "improved shine", "enhanced shine", and similar terms relating to increased shine means that untreated hair, when treated with one or more compounds and subjected to photographic image analysis techniques displays an increase in the reflection of light (e.g. increased gloss and sheen) as compared to identical or similar hair untreated with the same compound or compounds.

As used herein the term "dimethicone" means an optionally substituted polydimethylsiloxane (PDMS) comprising M siloxide units (($CH_3$)$_3$SiO—) at its ends. Additionally, unless indicated otherwise in this specification or the claims, as used herein a "dimethicone" may also refer to a cyclomethicone, having the formula [($CH_3$)$_2$SiO$_n$].

As used herein, the term "dimethiconol" means an optionally substituted polydimethylsiloxane having a hydroxyl group, rather than a methyl group, at each end.

Unless otherwise indicated, each and every range of values (concentrations, viscosities, and the like) stated in this specification, including the claims, are intended to specifically include the entire range and not just the endpoint(s). For example, a range stated to be 0 to 10 is intended to disclose all whole numbers between 0 and 10 such as, for example 1, 2, 3, 4, etc., all fractional numbers between 0 and 10 to three significant figures, for example 1.5, 2.3, 4.57, etc., and the endpoints 0 and 10,as well as all subranges having these numbers as endpoints (such as the subranges "3 to 5" and "2.3 to 7.1"). Similarly, ranges expressed as "up to", "at least", "greater than" (or less than) a given value means the range of values extending between that value and, depending upon the context, the highest value possible or lowest value possible such as 100% (or 0%) when expressed as a percentage, or 360 or 0 when expressed as an angle. Such subranges also include all whole and fractional numbers to two significant figures between the given value and the highest (or lowest) possible value, as appropriate. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

As is described herein, polysiloxanes may be used in the compositions of the invention. These include such compounds as dimethicone and dimethiconol, which differ by their end caps, wherein:

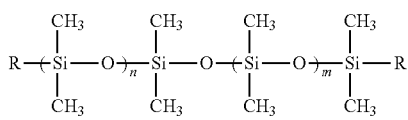

n and m are each 1 or more, and wherein the structure is dimethicone when R=CH$_3$ and the structure is dimethiconol when R=OH. Viscosity increases with increasing chain length, with a preferred range of viscosities ranging from about 0.65 cSt to >3 million cSt.

Unless otherwise indicated, a dimethiconol having an otherwise identical or substantially identical structure as a given dimethicone may be substituted for the given dimethicone in the compositions of the present invention, and vice versa.

Dimethicones, dimethiconols and their derivatives may have various or multiple functions in the compositions disclosed herein.

As carrier components; the volatile, low viscosity dimethicone(s), dimethiconol(s), phenyl silicone(s, or derivative(s) thereof may impart spreadability without a greasy or waxy feeling. Such compounds may include, or be selected from a trisiloxane, a tetrasiloxane and a pentasiloxane, including linear, cyclic, and phenyl derivatives thereof, and may include low molecular weight dimethicone, contained in preparations such as (identified by their viscosities): 1 cSt, 1.5 cSt, 2 cSt, and as impurities in non-homogeneous siloxane preparations, such as dimethicone (5 cSt) and dimethicone (6 cSt). These may be used alone or in combination with one or more volatile hydrocarbon or alcohol.

Non-volatile, higher molecular weight polysiloxanes such as dimethicones, dimethiconols, and phenyl silicones, as well as derivatives and mixtures thereof, may be used in some embodiments of the present invention as additional frizz-reduction agents, hair shine components and aesthetic modifiers. Such components may be divided into "lower viscosity" (low molecular weight) siloxane components, for example having a viscosity of between 6 to 5000 cSt; "intermediate viscosity" (intermediate molecular weight) siloxane components, for example having a viscosity between 5000 to 60,000 cSt; and "high viscosity" (high molecular weight) siloxane component, for example having a viscosity >60,000 cSt. Moreover, siloxane components of differing molecular weight and/or structure may be mixed to achieve compositions having a desired viscosity, and/or balance of frizz reduction, hair shine, aesthetic desirability, and manageability. Furthermore, some polysiloxane derivatives may comprise co-polymers or cross-polymers with groups such as fatty acid-containing moieties, alkenyl-containing moieties, and the like.

One or more additional components may be added to the compositions of the present invention. For example, such additives may, without limitation, include:

Colorants including, but not limited to, cosmetically approved silicone soluble dyes;

Hair shine ingredients, including but not limited to phenyltrimethicone, diphenylsiloxy phenyl trimethicone, diphenyl dimethicone, caprylic/capric triglycerides, mineral or natural oils, alkyl benzoates and the like. When oils or triglycerides are used in the present composition, their concentration is maintained low enough (e.g., less than about 10% or less than about 5% or less than about 2% or less than about 1.5%) to add shine to the hair without rendering the hair greasy or wet.

Sunscreen ingredients such as, without limitation, TiO$_2$ and zinc oxide to protect the hair from sunbleaching, discoloration or fading; such as for color-treated hair and to preserve hair color.

Aesthetic modifiers including, but not limited to, dimethicone crosspolymer, dimethicone/vinyl dimethicone crosspolymer, dimethicone/phenyl vinyl dimethicone crosspolymer, vinyl dimethicone/lauryl dimethicone crosspolymer, lauryl polydimethylsiloxyethyl dimethicone/bis-vinyl dimethicone crosspolymer, alkyl silicones, stearoxytrimethylsilane, ethylene-dimethicone copolymer, polyethylsiloxanes, alkyl silicones including caprylyl methicone, lauryl methicone and stearoxymethicone and the like.

Aesthetic modifiers may include thickener components, preservative components, fragrance components, pH adjustment components, plasticizer components, appearance modifiers or anti-oxidant components. Such aesthetic modifier components generally include ingredients which help to make delivery of the functional ingredients more acceptable by, for example, helping the active ingredients spread, diluting the active ingredients, stabilizing the active ingredients, and/or improving the look and feel of the composition when applied to the hair.

[In addition, there may also be other components effective in making the composition appealing to the consumer, such as (without limitation) essential oils, botanicals, scents, nucleic acids, specialty extracts, proteins, amino acids and vitamins. It will be apparent to the person of ordinary skill in the art in view of the present specification that low viscosity non-aerosol spray formulations of the present invention can also be applied as an aerosol using a propellant without loss of effectiveness.

In some embodiments, water-in-silicone or silicone-in-water emulsions can easily be made using an anhydrous anti-frizz concentrate as a base, then mixing the base with an aqueous phase preferably containing one or more emulsifying and stabilizing surfactant and occasionally a salt, and forming an emulsion. The emulsion may be a regular emulsion, formed by thorough mixing of the phases, may be formed as a water-in-oil emulsion which is then reversed to an oil-in-water emulsion by controlled addition of water, or may be a stable microemulsion appearing transparent or translucent. In certain cases, the refractive indices of the phases may be matched using a refractive index matching agent such as water or a glycol.

In other, less preferred, embodiments one or more of the components used in the hydrous compositions of the present invention may be separately provided in a dispersion or emulsion comprising a silicone phase containing such component or components and an aqueous phase. Two or more such dispersions or emulsions may, under certain circumstances be combined and further emulsified to create an emulsion equivalent to that created by using anhydrous compositions in the manner described above as a silicone phase "base" and mixing in a water phase.

Particularly, but not solely, when used as a concentrate or as part of an emulsion the compositions of the present invention may comprise a silicone-compatible non-volatile liquid carrier component.

Thus, in certain embodiments the present invention may comprise a silicone-in-water emulsion having a silicone phase, in which the silicone phase comprises
  a) at least 3.0%, by weight, of a polysiloxane fluid component selected from one or more of:
    i) an amodimethicone component, and
    ii) a polysiloxane component comprising a plurality of hindered amine side chains, and
  b) water.

In preferred, although non-exclusive, examples of the present invention, the composition of the present invention is a "leave-in" hair care product, which is applied to and left in the hair during the day or a part thereof. For example, the leave-in anti-frizz composition may be applied after shampooing the hair, and permitted to dry on the hair. In other leave-in applications the composition of the present invention may be sprayed or otherwise applied to the hair during the day as an aerosol or non-aerosol touch-up anti-fizz product.

The examples which follow are particular illustrations of the invention, which will be understood not to be limited thereby. The scope of the invention is defined solely by the claims.

DETAILED DESCRIPTION OF THE INVENTION

Figure 1A:
FIG. 1A shows the appearance of a hair tress treated with an aqueous emulsion containing dimethicone with hair tresses treated with anti-frizz compositions following exposure to 80% relative humidity and 80° F. for 6 hours.

The present invention is drawn to water-containing methods, compositions and uses for the reduction of hair frizz.

Preferred features of the invention will now be described.

In a preferred embodiment of the present invention there is provided a water-containing anti-frizz composition comprising:
a) at least about 3.0%, by weight, of a polysiloxane fluid component selected from one or more of:
  i) an amodimethicone component, and
  ii) a polysiloxane component comprising a plurality of hindered amine side chains;
b) an optional silicone-compatible, volatile or non-volatile liquid carrier component, and
c) water.

In another preferred embodiment of the present invention there is provided a water-containing anti-frizz composition comprising:
a) at least about 3.0%, by weight, of a polysiloxane fluid component selected from one or more of:
  i) an amodimethicone component, and
  ii) a polysiloxane component comprising a plurality of hindered amine side chains;
b) water.

Often the polysiloxane fluid component is dispersed as fine droplets in the carrier fluid; this will aid in distributing the polysiloxane fluid component evenly onto the hair.

Component a) may suitably be an amodimethicone (short for "amino-functionalized dimethicone"—a family of amino functionalized dimethicones and dimethiconols); which genus may include trimethyl silylamodimethicone, or an aminopropyl dimethicone. See the structure below:

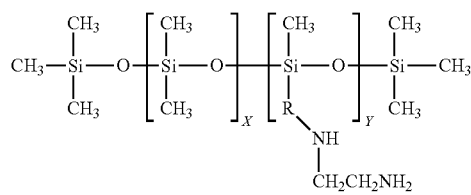

wherein X+Y is between about 50 to about 500 and R is a $C_3$ to $C_6$ alkylene group. Such compounds are sold by the Dow Corning Corp. under names such as DOW CORNING X2-8200, DOW CORNING X2-8107, Q2-8220, X2-8123, X2-8124, X2-8120, Softener CSF and X2-8130. In trimethyl silylamodimethicone, $R = -(CH_2)_3-$ in the structure immediately above. An aminopropyl dimethicone has the same dimethylsiloxane backbone structure with the pendant group being $-(CH_2)_3-NH_2$, and is also available from Dow Corning, Corp. In preferred embodiments, trimethylsilylamodimethicone and/or aminopropyl dimethicone may be used in conjunction, or in place of a polysiloxane component comprising a plurality of hindered amine side chains, as described below, in non-fizz compositions of the invention.

Component a) may therefore suitably comprise a polysiloxane component comprising a plurality of hindered amine side chains.

Such hindered amine side chains have the general formula (Formula 1), pendant from at least one Si atom in the polysiloxane side chain:

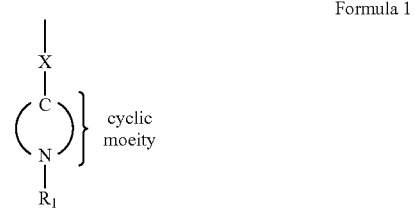

Formula 1 wherein $R_1$ is an H, OH, or a $C_1$-$C_5$ hydrocarbon; X is a $C_1$-$C_{10}$ hydrocarbon, a heteroatom, or

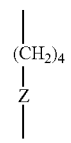

wherein Z is a heteroatom and d is 0 to about 6. Preferably Z is selected from N, O, S and P. In a preferred embodiment, Z is oxygen and d is about 3.

Preferably the cyclic moiety is a 5-membered ring or a 6-membered ring (e.g. a pyrrolidinyl ring or a piperidinyl ring), particularly preferably the cyclic moiety is a 6 membered ring.

The cyclic moiety of the side chain may be saturated, partly saturated, or unsaturated.

Preferably, the cyclic moiety is saturated. In preferred examples the side chain has the structure of Formula 2:

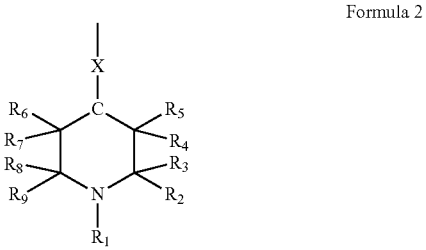

Formula 2 wherein $R_1$, $R_2$, $R_3$, $R_4$, $R_5$, $R_6$, $R_7$, $R_8$ and $R_9$ are independently an H, a $C_1$-$C_{10}$ hydrocarbon, an ester, a carboxyl or a halogen, and X is a $C_1$-$C_{10}$ hydrocarbon, a heteroatom, or

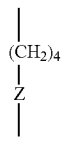

wherein Z is a heteroatom and d is 0 to about 6.

In some examples X is a $C_1$-$C_5$ hydrocarbon or a heteroatom such as a heteroatom selected from N, O, Si, P and S, preferably O. In other preferred examples, X is —$(CH_2)_d$—Z—, wherein Z is a heteroatom and d is 0 to about 6.

Preferably, d is from 1 to 4, most preferably 3.

Preferably Z is selected from N, O, S and P most preferably O.

In some preferred examples $R_1$ is H.

In some preferred examples $R_2$, $R_3$, $R_8$ and $R_9$ are each methyl.

In some preferred examples $R_4$, $R_5$, $R_6$ and $R_7$ are each H.

In some preferred examples $R_1$ is H and $R_2$, $R_3$, $R_8$ and $R_9$ are each methyl.

In some preferred examples $R_1$ is H and $R_2$, $R_3$, $R_8$ and $R_9$ are each methyl and X is —$(CH^2)_d$—Z—, wherein Z is a heteroatom preferably oxygen and d is 0 to about 6, preferably 1 to 4 preferably 3.

In a preferred example, $R_1$, $R_4$, $R_5$, $R_6$ and $R_7$ are H and $R_2$, $R_3$, $R_8$ and $R_9$ are methyl.

In a preferred example, $R_1$, $R_4$, $R_5$, $R_6$ and $R_7$ are H and $R_2$, $R_3$, $R_8$ and $R_9$ are methyl and X is —$(CH_2)_d$—Z—, wherein Z is a heteroatom preferably oxygen and d is 0 to about 6, preferably 1to 4 preferably 3.

A preferred polysiloxane component comprising a plurality of hindered amine side chains is an alkoxytetramethyl piperidinyl dimethicone; particularly preferably, propoxytetramethyl piperidinyl dimethicone (also called "HNH"). The structure of HNH is shown below, where m and n each is equal to or greater than 1; and in preferred preparations m+n is greater than 2, or greater than about 5, or greater than about 10, or greater than about 20, or greater than about 30, or greater than about 40, or greater than about 50, or greater than about 40, or greater than about 50. Preferably, m+n is less than about 700 or less than about 600, or less than about 500, or between about 50 and about 500.

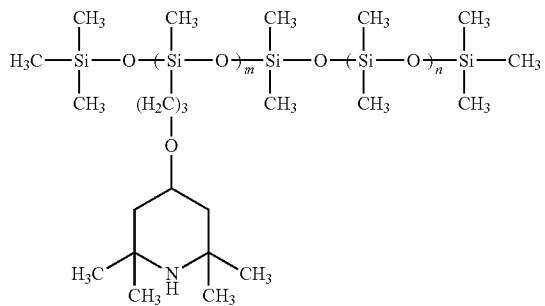

Such polysiloxane hindered amine compounds, including the preferred alkoxytetramethyl piperidinyl dimethicone component, may be prepared or obtained in a range of molecular weights having a range of viscosities such as from 10 cP to 1 million cP, preferably 100 cP to 100,000 cP; for example, one preparation may have a viscosity of about 200 cP, while another preparation may have a viscosity of about 10,000 cP, while yet another preparation may have a viscosity of about 30,000 cP or 90,000 cP. Blends of HNH preparations having different viscosities may be made to aid in rendering a composition having a desired final viscosity.

Component a) may suitably be a polysiloxane component comprising a plurality of hindered amine side chains comprising one or more of a piperidinyl moiety and/or a pyrrolidinyl moiety. In some examples, component a) comprises a polysiloxane component comprising at least two, or a plurality of, side chains, in which at least one side chain comprises a piperidinyl moiety, and another side chain comprises at least one pyrrolidinyl moiety.

Suitably, in some examples component a) may comprise a combination of one or more polysiloxane hindered amine compounds and one or more amodimethicones.

In some examples component a) may contain a polysiloxane component that comprises both an amodimethicone-type side chain and a plurality of hindered amine side chains as part of a single molecule.

The preferred compositions of the present invention comprises at least 3%, or at least about 3.1%, or at least about 3.2% by weight, or at least about 3.3% by weight, or at least about 3.4% by weight; preferably at least about 3.5%, or at least about 3.6%, or at least about 3.7% or at least about 3.8% or at least about 3.9% or at least about 4.0%, or at least about 4.1%, or at least about 4.2% by weight, or at least about 4.3% by weight, or at least about 4.4% by weight; preferably at least about 4.5%, or at least about 4.6%, or at least about 4.7% or at least about 4.8% or at least about 4.9% or at least about 5.0% by weight of polysiloxane fluid component a). Preferably the composition comprises up to about 25%, or up to about 20%, or up to about 18% or up to about 15% by weight of polysiloxane fluid component a).

Component b) is a silicone-compatible, volatile liquid carrier component. Component b) is optional, but may be preferred to aid spreadability of the polysiloxane fluid component a) on the hair. Component b) may comprise one or more components independently selected from a low molecular weight, volatile siloxy component, a volatile hydrocarbon, and a volatile alcohol.

Component b) provides a volatile or non-volatile liquid carrier for the nonvolatile components of the anti-fizz compositions herein, including component a) and other components described herein.

In some embodiments, component b) may comprise a silicone-compatible, volatile liquid carrier component comprising a volatile siloxy component selected from a dimethicone, a dimethiconol, a phenyl methicone, a phenyl methiconol, a phenyl trimethicone, a diphenyl dimethicone, a phenyl dimethicone, and a diphenylsiloxy phenyl trimethicone, a hexamethylsiloxane, a disiloxane, a trisiloxane, cyclotetrasiloxane, cyclopentasiloxane, cyclohexasiloxane, and a mixture of two or more of these components. Typically, the volatile siloxy component will have a viscosity of less than 6 cSt; for example between 0.65 cSt to 3 cSt; such as 1 cSt to 3 cSt. Generally, commercially available preparations of siloxy components within these viscosity ranges contain a distribution of lower and higher viscosity components centered around the stated viscosity of the siloxy component. Siloxy components of 0.65 cSt to 2 cSt are volatile; siloxy component preparations of 3 cSt may be partially volatile.

In some embodiments component b) may comprise a silicone-compatible, volatile liquid carrier component comprising a volatile hydrocarbon, such as isododecane.

In some embodiments component b) may comprise a silicone-compatible, volatile liquid carrier component comprising a volatile alcohol, such as methanol, ethanol, isopropanol or mixtures thereof.

In some examples the silicone-compatible, volatile liquid carrier component b) may comprise a siloxy component and a hydrocarbon component; a siloxy component and an alcohol component; an alcohol component and a hydrocarbon component; or a siloxy component, an alcohol component and a hydrocarbon component.

Thus, in one preferred embodiment, of the present invention there is provided a hydrous anti-fizz composition comprising:
  a) at least about 3.0%, by weight, of a polysiloxane fluid component selected from one or more of:
    i) an amodimethicone component, and
    ii) a polysiloxane component comprising a plurality of hindered amine side chains;
  b) optionally, a silicone-compatible, volatile or non-volatile liquid carrier component selected from: a low molecular weight, volatile siloxy component; a hydrocarbon; and an alcohol, and
  c) water.

Preferably the polysiloxane fluid component is present in an amount from at least 3%, or at least about 3.1%, or at least about 3.2% by weight, or at least about 3.3% by weight, or at least about 3.4% by weight; preferably at least about 3.5%, or at least about 3.6%, or at least about 3.7% or at least about 3.8% or at least about 3.9% or at least about 4.0%, or at least about 4.1%, or at least about 4.2% by weight, or at least about 4.3% by weight, or at least about 4.4% by weight; preferably at least about 4.5%, or at least about 4.6%, or at least about 4.7% or at least about 4.8% or at least about 4.9% or at least about 5.0%, or at least about 10%, by weight. In some embodiments the polysiloxane fluid component is present in an amount up to about 15% by weight, or to about 18% by weight, or about 20% by weight.

The optional silicone-compatible, volatile liquid carrier component is preferably present in an amount from about 22% by weight, to about 97.5% by weight.

Optionally, an alkylsiloxysilicate component is present at a concentration between 0% and about 15% by weight.

Optionally, particularly (although not exclusively) for serums, a non-volatile dimethicone and/or dimethiconol component having a viscosity of greater than 60,000 cP is present in an amount of from about 3% by weight to about 15% by weight. In certain cases the dimethicone or dimethiconol component may be comprised in a co-polymer or cross-polymer.

Optionally, particularly (although not exclusively) for low viscosity anti-frizz serum spritz or spray blends a non-volatile dimethicone and/or dimethiconol component having a viscosity of between about 5 cSt and about 1000 cP is present in an amount of from about 0.1% by weight to about 20% by weight. In certain cases, the dimethicone or dimethiconol component may be comprised in a co-polymer or cross-polymer.

In another preferred embodiment of the present invention there is provided a hydrous anti-fizz composition comprising:
  a) at least about 3.0%, by weight, of a polysiloxane fluid component selected from one or more of:
    i) an amodimethicone component, and
    ii) a polysiloxane component comprising propoxytetramethyl piperidinyl dimethicone component; and
  b) optionally, a silicone-compatible, volatile or non-volatile liquid carrier component selected from: a dimethicone, a dimethiconol, a phenyl methicone, a phenyl methiconol, a phenyl trimethicone, a diphenyl dimethicone, a phenyl dimethicone, and a diphenylsiloxy phenyl trimethicone, a hexamethylsiloxane, a disiloxane, a trisiloxane, cyclotetrasiloxane, cyclopentasiloxane, cyclohexasiloxane, isododecane, methanol, ethanol, isopropanol or mixtures of two or more of these components, and
  c) water.

Preferably the polysiloxane fluid component is present in an amount from at least 3%, or at least about 3.1%, or at least about 3.2% by weight, or at least about 3.3% by weight, or at least about 3.4% by weight; preferably at least about 3.5%, or at least about 3.6%, or at least about 3.7% or at least about 3.8% or at least about 3.9% or at least about 4.0%, or at least about 4.1%, or at least about 4.2% by weight, or at least about 4.3% by weight, or at least about 4.4% by weight; preferably at least about 4.5%, or at least about 4.6%, or at least about 4.7% or at least about 4.8% or at least about 4.9% or at least about 5.0%, or at least about 10%, by weight. In some embodiments the polysiloxane fluid component is present in an amount up to about 15% by weight, or to about 18% by weight, or about 20% by weight.

The silicone-compatible, volatile liquid carrier component is preferably present in an amount from about 0.5% by weight, to about 97.5% by weight.

Optionally, an alkylsiloxysilicate component is present at a concentration from greater than 0% to about 15% by weight.

Optionally, particularly (although not exclusively) for serums, a non-volatile dimethicone and/or dimethiconol component having a viscosity of greater than 60,000 cP is present in an amount of from about 3% by weight to about 15% by weight. In certain cases the dimethicone or dimethiconol component may be comprised in a co-polymer or cross-polymer.

Optionally, particularly (although not exclusively) for low viscosity anti-frizz serum spritz or spray blends a non-volatile dimethicone and/or dimethiconol component having a viscosity of between about 5 cSt and about 1000 cP is present in an amount of from about 0.1% by weight to about 20% by weight. In certain cases, the dimethicone or dimethiconol component may be comprised in a co-polymer or cross-polymer.

If present, the optional alkylsiloxysilicate component may preferably comprise a trimethylsiloxysilicate component, a phenylpropyldimethylsiloxysilicate component or mixtures thereof. Most preferably, the alkylsiloxysilicate component comprises a trimethylsiloxysilicate component.

In preferred examples, the alkylsiloxysilicate component comprises a trimethylsiloxysilicate-based Q resin silicone polymer, known also as MQ resin. Trimethylsiloxysilicate has the basic structure $(CH_3)_3$—Si—O—Si—$(OH)_3$; the $(CH_3)_3$—Si—O unit is known as an "M" unit, while $SiO_4$ is known as a "Q" unit. An MQ resin is built from M and Q units to form a branched, cage-like oligosiloxane structure that is insoluble in water. Such resins are known to those skilled in the art and are available from Dow Corning Corp. and sold under trade names including DOW CORNING MQ-1600 and DOW CORNING MQ-1640.

Thus in one preferred embodiment, of the present invention there is provided a hydrous anti-fizz composition comprising:
  a) at least about 3.0%, by weight, of a polysiloxane fluid component selected from one or more of:
    i) an amodimethicone component, and
    ii) a polysiloxane component comprising a plurality of hindered amine side chains; and b) optionally, a silicone-compatible, volatile liquid carrier component,
c) a trimethylsiloxysilicate-based resin silicone polymer, and
d) water.

Preferably the polysiloxane fluid component is present in an amount from at least 3%, or at least about 3.1%, or at least about 3.2% by weight, or at least about 3.3% by weight, or at least about 3.4% by weight; preferably at least about 3.5%, or at least about 3.6%, or at least about 3.7% or at least about 3.8% or at least about 3.9% or at least about 4.0%, or at least about 4.1%, or at least about 4.2% by weight, or at least about 4.3% by weight, or at least about 4.4% by weight; preferably at least about 4.5%, or at least about 4.6%, or at least about 4.7% or at least about 4.8% or at least about 4.9% or at least about 5.0%, or at least about 10%, by weight. In some embodiments the polysiloxane fluid component is present in an amount up to about 15% by weight, or to about 18% by weight, or about 20% by weight.

The silicone-compatible, volatile liquid carrier component is preferably present in an amount from about 0.5% by weight, to about 97.5% by weight.

The alkylsiloxysilicate component is preferably present at a concentration from greater than 0% to about 15% by weight.

Particularly (although not exclusively) for, a non-volatile dimethicone and/or dimethiconol component having a viscosity of greater than 60,000 cP may be present in an amount of from about 3% by weight to about 15% by weight. In certain cases the dimethicone or dimethiconol component may be comprised in a co-polymer or cross-polymer.

Particularly (although not exclusively) for low viscosity [anti-frizz spritzer spray blends a non-volatile dimethicone and/or dimethiconol component having a viscosity of between about 5 cSt and about 1000 cP may be present in an amount of from about 0.1% by weight to about 20% by weight. In certain cases, the dimethicone or dimethiconol component may be comprised in a co-polymer or cross-polymer.

Thus, in some preferred embodiments the invention provides a hydrous anti-frizz composition comprising:
a) at least 3.0%, by weight, of a polysiloxane fluid component selected from one or more of:
  i) an amodimethicone component, and
  ii) a polysiloxane component comprising a plurality of hindered amine side chains; and
b) a silicone-compatible liquid carrier component,
c) a trimethylsiloxysilicate-based resin silicone polymer,
d) a nonvolatile component selected from one or more of dimethicone, dimethiconol and phenyl silicone, and
e) water.

The nonvolatile component d) may comprise a single component, or a mixture of components, and may have a viscosity ranging from about 6 cSt to several million cSt.

The nonvolatile component d) may comprise one or more of dimethicone, dimethiconol and phenyl silicone components typically referred to as low viscosity (low molecular weight) for example having a viscosity of between 6 to 5000 cSt, intermediate viscosity (intermediate molecular weight) for example having a viscosity between 5000 to 60,000 cSt, high viscosity (high molecular weight) for example having a viscosity >60,000 cSt. The non-volatile component may be present as part of a cross-polymer or co-polymer.

In embodiments in which component d) comprises one or more of a high viscosity dimethicone, dimethiconol and phenyl silicone components, the viscosity may be between 60,000 cSt and several million cSt. In some embodiments the viscosity may be between 60,000 cSt and 4 million cSt. In some embodiments, the viscosity may be between 60,000 cSt and 35 million cSt for example when using high molecular weight gums, such as dimethicone gum, or dimethiconol gum.

In embodiments wherein component d) comprises one or more phenyl silicones, the phenyl silicone may include phenyl methicones, phenyl methiconols, phenyl trimethicones, diphenyl dimethicones, phenyl dimethicones, and diphenylsiloxy phenyl trimethicones.

In some embodiments, component b) provides a liquid carrier for the non-volatile anti-frizz components comprising component a), optional component c), and/or optional component d).

Thus, in some embodiments of the invention low molecular weight, volatile dimethicone components such as hexamethylsiloxane, disiloxane and/or trisiloxane may be comprised in the volatile carrier for the non-volatile anti-frizz components (non-volatile polysiloxanes and/or trimethylsiloxysilicate and hindered amine siloxanes such as propoxytetramethyl piperidinyl dimethicone.

The high viscosity polysiloxane component thickens the anti-frizz serum for application control, application aesthetics, and additionally so that it may form a film or coating on the hair fiber. When formulated with a silicone-compatible, non-aqueous volatile carrier the polysiloxane component applies smoothly and provides an excellent hair feel after the carrier evaporates.

When formulated in a composition at higher concentrations, the high viscosity polysiloxane component, particularly when combined with trimethylsiloxysilicate, unexpectedly also aids in increased curl definition and curl memory is also retained under high humidity conditions when 1.5 gram tresses are treated with the composition and evaluated at 80° F. and 80% humidity for 6 hours.

While not wishing to be limited by theory, greater curl definition and curl memory is thought to be achieved by removing water from the cortex of the hair shaft during application and/or preventing water from being taken up by the hair and also by reducing the hair fiber-to-hair fiber friction, thus permitting the hair shafts to align against each other and causing an increase in curl definition.

Dimethicones of low and intermediate viscosity, such as a viscosity between about 6 cSt to 60,000 cSt can be used as instead of, or in combination with the high molecular weight siloxanes (e.g. dimethicone or dimethiconol) to keep the viscosity of the anti-frizz serum, spritz or spray within the desired viscosity for their intended use; serums are commonly used after shampooing and/or conditioning as a leave-in agent, while sprays and "spritzes" are generally used as a touchup during the day.

Phenyl silicones such as phenyl methicones, phenyl methiconols, phenyl trimethicones, diphenyl dimethicones, phenyl dimethicones, and diphenylsiloxy phenyl trimethicones and the like can used in place of, or in combination with, either high, intermediate, or low viscosity dimethicone, dimethiconols, volatile hydrocarbons and/or alcohols in, for example, low viscosity applications. Like the siloxanes described above, these materials can improve the ease of application ("spreadability") of the composition on the hair and improve hair shine.

In some embodiments, the composition of the present invention may optionally contain one or more additional ingredients. For example, the additional ingredient may comprise one or more components selected from the group consisting of:

a colorant component (such as a cosmetically approved silicone-soluble dye), a hair shine ingredient (such as one or more ingredient selected from phenyltrimethicone, diphenylsiloxy phenyl trimethicone, diphenyl dimethicone, caprylic/capric triglycerides, mineral or natural oils, and alkyl benzoates), a sunscreen ingredient (such as titanium oxide and zinc oxide), an aesthetic modifier component (e.g., thickener components, preservative components, fragrance components, pH adjustment components, plasticizer components, appearance modifiers and/or anti-oxidant components). Such agents may include one or more of the following medium to high molecular weight silicone components: dimethicone crosspolymer, dimethicone/vinyl dimethicone crosspolymer, dimethicone/phenyl vinyl dimethicone crosspolymer, vinyl dimethicone/lauryl dimethicone crosspolymer, lauryl polydimethylsiloxyethyl dimethicone/bis-vinyl dimethicone crosspolymer, alkyl silicones, stearoxytrimethylsilane, ethylene-dimethicone copolymer, polyethylsiloxanes, alkyl silicones including caprylyl methicone, lauryl methicone and stearoxymethicone,

- an essential oil component,
- a botanical component,
- a scent component,
- a nucleic acid component,
- a specialty extract component, and
- a vitamin.

In some embodiments, the methods and compositions disclosed herein may be used on hair that has not been artificially dyed or pigmented.

In other embodiments, the methods and compositions disclosed may be used on hair that has been artificially dyed or pigmented, for example to retain hair color.

In some presently less preferred examples the compositions of the present invention may comprise a polysiloxane component in combination with a detersive component (for example, as a component of a "conditioning shampoo" formulation); while in other, more preferred, examples the compositions of the present invention are not formulated in a shampoo formulation or used to clean hair or skin, and even more preferably, lack a detersive component. By a "detersive component" is meant a composition comprising a surfactant concentration is effective to clean dirt or oil from skin or hair when used as an ordinary soap or shampoo.

In some examples, the compositions of the present invention may cause a reduction in hair frizz at 80° F. and 80% humidity relative to untreated otherwise identical frizzy hair under the same temperature and humidity conditions.

A preferred method for measuring the reduction in hair fizz is the High Humidity Frizz Control Test Method defined in the examples. In this application a reduction in hair frizz is suitably measured using this test, relative to untreated frizzy hair under the same temperature and humidity conditions, preferably at a temperature of 80° F. and 80% humidity.

In some embodiments, the compositions of the present invention may cause at least a 70% reduction in hair frizz at 80° F. and 80% humidity relative to untreated otherwise identical frizzy hair under the same temperature and humidity conditions.

In some embodiments, the compositions of the present invention may cause at least a 75% reduction in hair frizz at 80° F. and 80% humidity relative to untreated otherwise identical frizzy hair under the same temperature and humidity conditions.

In some embodiments, the compositions of the present invention may cause at least an 80% reduction in hair frizz at 80° F. and 80% humidity relative to untreated otherwise identical frizzy hair under the same temperature and humidity conditions.

In some embodiments, the compositions of the present invention may cause at least an 85% reduction in hair frizz at 80° F. and 80% humidity relative to untreated otherwise identical frizzy hair under the same temperature and humidity conditions.

In some embodiments, the compositions of the present invention may cause at least a 90% reduction in hair frizz at 80° F. and 80% humidity relative to untreated otherwise identical frizzy hair under the same temperature and humidity conditions.

In some embodiments, the compositions of the present invention may cause at least a 95% reduction in hair frizz at 80° F. and 80% humidity relative to untreated otherwise identical frizzy hair under the same temperature and humidity conditions.

In the some embodiments of the present invention there is provided a method of reducing or preventing hair frizz, comprising the steps:

I) applying to hair a composition as described herein; and
II) distributing said composition along a plurality of hair shafts.

In another embodiment of the present invention there is provided the use of a composition as described herein to reduce hair frizz.

In a preferred embodiment, the present invention provides a method of reducing or preventing hair frizz, comprising the steps:

I) applying to hair a composition as described herein; and
II) distributing said composition along a plurality of hair shafts;

wherein the reduction in hair frizz is measured relative to untreated frizzy hair under the same temperature and humidity conditions.

In a preferred embodiment the present invention provides the use of a composition as described herein to reduce hair frizz; wherein the reduction in hair frizz is measured relative to untreated frizzy hair under the same temperature and humidity conditions.

The further examples provided below are intended to illustrate various embodiments of the invention, and are not intended to limit the scope of any claim. Hence it is the claims alone that define the scope of the invention, including any equivalents thereof.

In one example the invention is directed to a leave-in anti-frizz cationic oil-in-water emulsion comprising a) a first component comprising at least 3.0%, by weight, of a polysiloxane fluid component selected from one or more of:
  i) an amodimethicone component, and
  ii) a polysiloxane component comprising a plurality of hindered amine side chains;
b) a second component comprising one or more of:
  i) a fatty alcohol,
  ii) a fatty quaternium salt, and
  iii) a fatty amine.

Suitable fatty quaternary ammonium salts, include but are not limited to: cetrimonium chloride, stearalkonim chloride, behentrimonium chloride (also known as docosyltrimethylammonium chloride), behentrimonium methosulfate, dicetyldimonium chloride (also known as diceyl dimethyl ammonium chloride), hydroxypropyltrimonium chloride, ricinoleamidopropyltrimonim chloride ricinoleamidopropyltrimonim ethosulfate, ricinoleamidopropyltrimonim methosulfate, saffloweramidopropyl ethyldimonium ethosulfate, quaternized stearamidopropyl amine, and the like and mixture thereof.

Fatty alcohols are commonly used in the oil phase of cationic oil-in-water emulsions. They, along with the fatty quaternium salt(s), provide enhanced combing and silky hair feel, and also contribute to the viscosity of the emulsion. Suitable fatty alcohols include, but are not limited to, lauryl alcohol, cetyl alcohol, stearyl alcohol, behenyl alcohol and mixtures thereof.

Fatty alcohol derivatives, such as esterification products of a fatty alcohol and a polyethylene glycol (e.g., the Laureth, Trideceth and Pareth "PEGylated" products), may often be used in water-in-oil or oil-in-water emulsion as an emulsifier, solubilizing agent and a non-ionic surfactant.

In some cases, a water-soluble thickener may be used to control the viscosity of the emulsion to provide both an acceptable viscosity and enhance the stability of the emulsion. Suitable water soluble thickeners include, cellulose-based thickeners, guar gum, cassia gum, locust bean gum, xanthan gum, acacia senegal gum, caesalpina spinosa gum, clays such as silica, bentonite, and magnesium aluminum silicate), acrylamidopropyltrimonium chloride/acrylates copolymers, derivatized and underivatized Carbomers, organically modified clays, such as quaternized clays, and the like, and mixtures thereof. In one example the invention is directed to a water-containing cationic emulsion comprising: water, a fatty quaternized salt, a fatty alcohol, a ethoxalated fatty alcohol, a phenyl-modified silicone, a carrier containing an alcohol, volatile silicone and/or a volatile hydrocarbon; a dimethicone having a viscosity of between about 1 cSt (centistokes) and about 5000 cSt; an alkylsiloxysilicate such as trimethylsiloxysilicate; and a propoxytetramethyl piperidinyl dimethicone component, preferably having a viscosity of from about 200 cSt to about 100,000 cSt. Such an emulsion is suitable for use as a leave-in anti-frizz conditioner or a combing creme.

In this example, the invention is directed to a water-containing cationic emulsion that provides greater than 70%, or 75%, or 80% reduction of hair frizz caused by high humidity, said composition comprising an emulsion containing an anti-fizz component selected from the group consisting of: greater than 3%, or greater than about 3.1%, or greater than about 3.2%, or greater than about 3.3%, or greater than about 3.4%, or greater than about 3.5%, or greater than about 4%, or greater than about 5%, or greater than about 10%, or greater than about 15%, by weight, of a propoxytetramethyl piperidinyl dimethicone component. Generally, but not invariably, the upper concentration range limit of the anti-fizz component (e.g., an amodimethicone or a polysiloxane component comprising a plurality of hindered amine side chains) is about 20%, or about 18%, or abut 15%, or about 12%, or about 10%, or about 8%, by weight.

Additional examples are disclosed below; a person of ordinary skill in the art will, in light of such disclosure, be immediately aware of numerous additional examples within the scope of the claims.

EXAMPLES

In all examples given below, amounts of the various formulation components are given in weight percent, unless specifically indicated otherwise.

High Humidity Frizz Control Test Method

Approximately 1.5 grams (weight of the hair) curly hair (Brazilian) [International Hair Importers; 8729 Myrtle Ave; Glendale, N.Y. 11385] is pre-washed 2× with a 10% by weight SLES-2 (sodium lauryl ethoxy sulfate having an average of 2 moles of ethylene oxide) solution in water. The wet hair tresses are hung overnight in a temperature/humidity chamber set at 80° F./80% relative humidity (RH).

Tresses are then removed from the chamber, coded and photos are taken with a high-resolution camera. Pictures are used as a baseline for initial frizz value analysis using image analysis software permitting numerical analysis of the optical properties of curly, frizzy, and African hair types, and measurement of hair fiber alignment with 2-D Fourier transform. [Image-Pro Plus® version 7.0; Media Cybernetics, Inc., 4340 East-West Highway, Suite 400, Bethesda, Md. 20814].

After the pictures are taken, tresses are pre-wet under running water for 10 seconds and towel dried. 50 μl of each test formulation is hand-applied to the tress from the root end down. The test formulation is distributed as evenly as possible along the hair.

After the application of a test formulation, the tresses are hung in the humidity chamber set at 80° F. (27° C.)/80% RH for 6 hours.

Post-treatment photos of the hair are taken. Pre- and post-treatment photos are used in conjunction with the Image Pro Plus® software. Photos are used to compare these images and analyze the reduction in frizz values in the treated tresses (frizz protection) vs. the frizz values of the untreated, humidified tresses to obtain numerical values for percent frizz reduction.

Example A

Formulations of some commercially available anti-frizz products were purchased and evaluated for frizz control and are represented in Table A, below.

TABLE A

| | Formulation A Serum | Formulation B Serum | Formulation C Serum |
|---|---|---|---|
| | Cyclopentasiloxane Dimethicone Capric and Caprylic Triglycerides Dimethiconol Fragrance and other inactive ingredients* | Cyclopentasiloxane Dimethicone Dimethiconol Mineral oil Fragrance and other inactive ingredients* | Cyclopentasiloxane Dimethiconol Mineral oil Fragrance and other inactive ingredients* |
| % Frizz Reduction | 75% | 70% | 68% |
| % Solids | 35.47% | 14.46% | 15.54% |

| | Formulation D Anhydrous Spray | Formulation E Water Based Emulsion Spray |
|---|---|---|
| | Alcohol Cyclopentasiloxane Bis-phenylpropyl Dimethicone Dimethicone C12-15 Alkyl Benzoate Fragrance and other inactive ingredients | Water Cetearyl Alcohol Behentrimonium Chloride Propylene Glycol Cyclomethicone Fragrance and other inactive ingredients |

TABLE A-continued

| | | |
|---|---|---|
| % Frizz Reduction | 30% | 17% |
| % Solids | 6.27% | 5.30% |

Formulation A contains capric/caprylic triglycerides, a purified, fractionated derivative of coconut oil. Formulations B and C include mineral oil. As discussed previously, oils have both practical and aesthetic disadvantages. They tend to stain fabrics (such as clothing, sheets, pillowcases), have a heavy feel and may leave hair with an undesired slicked, "wet" appearance. Only Formulation E is water-based, and this formulation, which is marketed as an anti-frizz formulation, is actually unable to show frizz reduction greater than 17% activity.

Example 1

Two emulsion formulations were made as follows:

TABLE 1

| Ingredient | A wt % | B wt % |
|---|---|---|
| dimethicone (60,000 cSt) | 50.0 | — |
| propoxytetramethyl piperidinyl dimethicone | — | 50.0 |
| Laureth-4* | 3.0 | 3.0 |
| Laureth-23* | 3.0 | 3.0 |
| water | 44.0 | 44.0 |

*Laureth-4 and Laureth-23 are synthetic polymers composed of lauryl alcohol and PEG (polyethylene glycol); they differ by the number of ethylene oxide residues per mole.

From each of these formulations test anti-frizz formulations were made as follows:

TABLE 2

| Ingredient | Test 1 wt % | Test 2 wt % |
|---|---|---|
| Deionized Water | 90.0 | 90.0 |
| Emulsion A from Table 1 | 10.0 | — |
| Emulsion B from Table 1 | — | 10.0 |

Figure 1B:
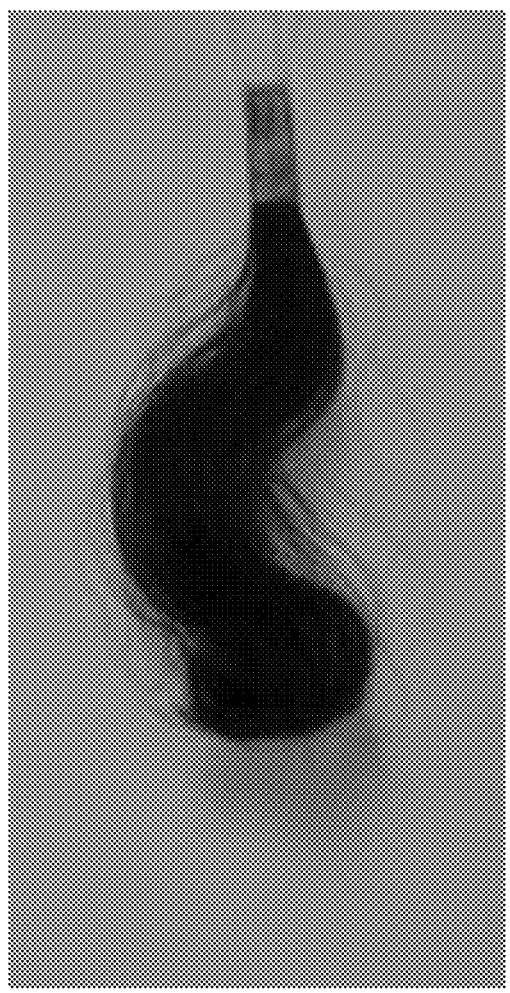
FIG. 1B shows the appearance of a hair tress treated with an aqueous emulsion containing propoxytetramethyl piperidinyl dimethicone following exposure to 80% relative humidity and 80° F. for 6 hours.
Figure 1C:
FIG. 1C shows the appearance of an untreated, washed hair tress following exposure to 80% relative humidity and 80° F. for 6 hours.

Three substantially identical frizzy hair tresses of Brazilian origin were washed as set forth above in the description of the High Humidity Frizz Control Test Method and Formulations Test 1 (containing 5 wt % dimethicone) and Test 2 (containing 5 wt % propoxytetramethyl piperidinyl dimethicone) were then applied and distributed to each of two of these tresses while the hair was wet; the third tress was untreated. The three tresses were hung overnight in a temperature/humidity chamber set at 80° F./80% relative humidity (RH), and the tresses were assessed then assessed as set forth in the description of the High Humidity Frizz Control Test Method for percent frizz reduction as compared to the untreated control tress (FIG. 1C). The use of dimethicone in the Test 1 formulation only provided 66% frizz reduction in the treated tress (FIG. 1A), while the use of propoxytetramethyl piperidinyl dimethicone in the Test 2 formulation provided 80% fizz reduction in the treated tress (FIG. 1B).

Example 2

Two test formulations (Test Formulation A and Test Formulation B) containing propoxytetramethyl piperidinyl dimethicone were made as follows:

TABLE 3

| Ingredient | A wt % | B wt % |
|---|---|---|
| Water | 90 | 75 |
| HNH-HV 50% active emulsion* | 10 | 0 |
| Microsil ® HAF** | 0 | 25 |

*HNH-HV emulsion consists of 50% propoxytetramethyl piperidinyl dimethicone in water emulsified with Laureth-4 and Laureth-23.
**Microsil HAF consists of a microemulsion of 20% propoxytetramethyl piperidinyl dimethicone in water, with Trideceth-6 and C11-15 Pareth-7.

These test formulations were applied to frizzy hair and the resulting tresses were subjected to High Humidity Frizz Control Test Method, then the frizz reduction was determined as described in Example 1.

| | Test Form. A | Test Form. B |
|---|---|---|
| Frizz reduction | 85% | 81% |
| Viscosity | ~75 cP | ~50 cP |

Example 3

Cationic oil-in-water formulations are made as shown in Table 4, below. Ingredients are given in weight percent; unless otherwise indicated, all concentration percentages given in this patent application are weight percentages. Generally speaking, cationic oil-in-water emulsions contain water, a cationic fatty quaternium emulsifier and an oil phase. The cationic oil-in-water emulsions are formed by the following processes:
1) Water is added to a container suitable to allow the subsequent addition of the oil phase. Add and mix together the hydrophilic ingredients of the formula in the water until uniform. If necessary to solubilize all the hydrophilic components, the water phase is heated to a temperature slightly higher than the melting temperature of the cationic emulsifier or the highest melting point material of the composition.
2) The cationic emulsifier, the hydrophobic ingredients and the amine functional silicone frizz control ingredient is added to the water, while maintaining a temperature of slightly higher than the melting point of highest melting point ingredient. The amine functional silicone frizz control ingredient may have a viscosity based on its intended use; thus, for example, if the end product is a lotion, the viscosity may be about 3000 cP; if the end product is a cream the viscosity may be about 10,000 cP; if the end product is a paste, the viscosity may be about 20,000 cP or more.
3) The mixture is cooled to a suitable temperature room temperature based on the temperature tolerance of the additional ingredients; some ingredients like volatile components, including fragrances; preservatives, or any material that breaks down at elevated temperature can be or should added after cool down.
4) The pH of the final product is then adjusted to a suitable or desired pH (usually between 3.5-5.5).

TABLE 4

| | Formulation | | | | | | |
|---|---|---|---|---|---|---|---|
| Ingredient | 1 | 2 | 3 | 4 | 5 | 6 | 7 |
| Water | 83.2 | 70.7 | 80.7 | 88.2 | 86.5 | 72.5 | 77.5 |
| Behentrimonium Metosulfate | 0.80 | 0.80 | 0.80 | 0.80 | 1.00 | 1.00 | 1.00 |

TABLE 4-continued

| Ingredient | Formulation | | | | | | |
|---|---|---|---|---|---|---|---|
| | 1 | 2 | 3 | 4 | 5 | 6 | 7 |
| Ceteareth-20 | 0.50 | 0.50 | 0.50 | 0.50 | | 0.50 | 0.50 |
| Cetearyl Alcohol | 3.00 | 3.00 | 3.00 | 3.00 | 3.00 | 3.00 | 3.00 |
| Propoxytetramethyl Piperidinyl Dimethicone | 2.50 | 5.00 | 5.00 | 7.5 | 6 | 3 | 3 |
| Cyclopentasiloxane | 10.00 | | | | | | |
| Cyclopentasiloxane (and) Dimethicone blend | | 20.00 | | | | | |
| Trimethylsiloxysilicate | | | 10.00 | | 10 | | |
| Dimethicone 100 cSt | | | | 6 | | | |
| Dimethicone (and) Dimethiconol | | | | | | | 15 |
| Phenyltrimethicone | | | | | 10 | | |

Each of the formulations 1-7 are found to have frizz reduction activity, when applied to tresses assessed using the High Humidity Frizz Control Test Method, have a frizz reduction activity greater than 70% as compared to an untreated control.

In separate tests, hair treated by combing each of Formulations 1 through 6 through the hair are found to show at least 70% frizz reduction relative to untreated tresses.

Example 4

Table 5 shows an set of anti-frizz compositions formulated as leave-in cationic emulsion sprays, having a reduced viscosity suitable for spraying relative to the combing creams of Formulations 1-7. This reduced viscosity is accomplished by reducing the use of fatty ingredients. Such compositions are not only suitable for use in a pump-style, non-aerosol spray applicator, but also as an aerosol by use of a propellant. Generally, the method of making such sprays is otherwise similar to the method of making the compositions of Formulations 1-7.

TABLE 5

| Ingredient | Formulation | | | | |
|---|---|---|---|---|---|
| | 8 | 9 | 10 | 11 | 12 |
| Water | 73.2 | 68.2 | 88.2 | 68.95 | 77.7 |
| Behentrimonium Metosulfate | 0.8 | 0.8 | 0.8 | 0.8 | 0.8 |
| Ceteareth-20 | 1 | 1 | 1 | 1.25 | 1.5 |
| Propoxytetramethyl Piperidinyl Dimethicone (and) Trideth-6 (and) C11-15 Pareth-7 20% active amine | 25 | 30 | 10 | 25 | 10 |
| Dimethicone (and) Laureth-3 (and) Laureth-23 50% active dimethicone | | | | 5 | 10 |

Hair lightly sprayed, then combed with one of Formulations 8 through 12 shows at least 70% frizz reduction relative to untreated tresses.

Example 5

Table 6 shows examples of leave-in, non-aerosol anti-frizz hair-styling mousse formulations. Each formulation is made by combining and mixing ingredients together in the order given:

TABLE 6

| Ingredient | Formulation | | |
|---|---|---|---|
| | 13 | 14 | 15 |
| Water | 62 | 67 | 72 |
| Glycerin | 2 | 2 | 2 |
| Cocamidopropyl betaine | 1 | 1 | 1 |
| 20% Propoxytetramethyl Piperidinyl Dimethicone in emulsion with Trideth-6 and C11-15 Pareth-7 | 25 | 30 | 10 |
| 50% Dimethicone (and) Laureth-4 (and) Laureth-23 | 10 | | 15 |

Cocamidopropyl betaine is a quaternary ammonium fatty carboxylic acid salt, used as surfactant and a foam agent.

Trideth-6 is a polyethylene glycol (PEG) ether of tridecyl alcohol, with 6 units of ethylene oxide in the molecule.

C11-15 Paneth-7 is a polyethylene glycol ether of a mixture of synthetic C11-15 fatty alcohols with an average of 7 moles of ethylene oxide.

Hair treated, then combed with one of Formulations 13 through 15 shows at least 70% frizz reduction relative to untreated tresses.

Example 6

The following leave-in, anti-frizz hair-styling mousse formulations are for use as a concentrate for aerosol use. The ingredients are added and mixed in the order presented in Table 7.

TABLE 7

| Ingredient | Formulation | | |
|---|---|---|---|
| | 16 | 17 | 18 |
| Water | 89.2 | 87.2 | 84.2 |
| Cocamidopropyl betaine | 2 | 2 | 2 |
| *Polyquaternium-11 | 1 | 1 | 1 |
| **Ammonium acrylates copolymer | 2.8 | 2.8 | 2.8 |
| Cyclopentasiloxane | 2.5 | | |
| Propoxytetramethyl Piperidinyl Dimethicone | 2.5 | 3.5 | 5.0 |
| Dimethicone (20 cSt) | | 3.5 | 3.5 |

*Polyquaternium-11 is a quaternary ammonium polymer formed by the reaction of diethylsulfate and a copolymer of vinyl pyrrolidone and dimethyl aminoethylmethacrylate.
**Ammonium Acrylates Copolymer is an ammonium salt of 2-methyl-2-propenoic acid polymer conjugated with 2-propenoic acid or one or more of their simple esters. It is an antistatic agent, a film forming agent and a viscosity-controlling product.

Hair treated, then combed with one of Formulations 16 through 18 shows at least 70% frizz reduction relative to untreated tresses.

Non-Ionic Oil-In-Water Emulsions

The oil-in-water emulsions of the present invention do not necessarily need to be cationic emulsions. Nonionic oil-in-water emulsions can also be used as a delivery vehicle or carrier for formulations of the invention. The advantage of these non-ionic emulsions is that a high viscosity amino functional silicone comes in direct contact with the hair and forms a better film on the hair to provide a higher level of frizz control.

Broadly speaking, the nonionic oil-in-water emulsions of the present invention contain water, a nonionic silicone emulsifier, and a silicone phase, as well as optional addition ingredients.

In a general scheme, nonionic oil-in-water emulsions may be formed by

1) Phase A: Adding the hydrophobic ingredients to a suitable container which is large enough to allow the later addition of the water phase ingredients. The hydrophobic ingredients are heated to a temperature slightly higher than the melting temperature of the ingredient having the highest melting temperature if require to melt solid ingredients, and mixed.

2) Phase B: In a separate container, mixing together the water and any other hydrophilic ingredients until uniform.

3) About 10% (wt) of Phase B is added and mixed with the hydrophobic ingredients of Phase A to form a uniform, thick water-in-oil paste.

4) The remaining aqueous hydrophilic phase is then slowly added to the water-in-oil emulsion with adequate mixing to invert the emulsion from a water-in-oil emulsion to a nonionic oil-in-water emulsion.

Suitable nonionic emulsifiers include, but not limited to ethoxylated aliphatic alcohols, secondary alcohol ethoxylates, polyoxyethylene surfactants, carboxylic esters, polyethylene glycol esters, anhydrosorbitol esters and derivatives, glycol esters of fatty acids, carboxylic amides, monoalkanolamine condensates, polyoxyethylene fatty acid amides and the like.

Fatty alcohols are commonly used in the oil phase of nonionic oil-in-water emulsions. They provide enhanced combing and hair feel and also contribute to the viscosity of the emulsion. Suitable fatty alcohols include, but are not limited to, lauryl alcohol, cetyl alcohol, stearyl alcohol, biphenyl alcohol, non-ionic derivatives thereof (e.g., those in which the fatty alcohol is conjugated to a non-polar polymeric group such as polyethylene glycol) and mixtures of any two or more of these.

In some cases, a water soluble thickener may be used to control the viscosity of the emulsion to provide both an acceptable viscosity and enhance the stability of the emulsion. These ingredients are typically added to the water phase, however in some formulations it may be better suitable to add them to the oil phase and hydrate upon the addition of the water phase. Suitable water soluble thickeners include, cellulosic thickeners, guar gum, cassia gum, locust bean gum, xanthan gum, acacia senegal gum, caesalpina spinosa gum, clays and organically modified clays, carbomers, acrylates/C10-30 alkyl acrylate crosspolymers, polyacrylamide, polyacrylamide/polyacrylate crosspolymer-6, hydroxyethyl acrylate/sodium acryloyldimethyl taurate copolymer, acrylamide/ammonium acrylate copolymer, polyacrylate-13, sodium acrylate/acryloyldimethyltaurate/dimethylacrylamide crosspolymer, acrylamide/sodium acryloyldimethyltaurate copolymer, sodium acrylate/acryloyldimethyltaurate/simethylacrylamide crosspolymer and the like.

One or more additional components may be added to any of the compositions of the present invention. For example, such additives may, without limitation, include one or more of the following:

Detangling aids including:
Non-fatty quaternary ammonium conditioning and detangling agents including, but not limited to, polyquaterniums, cationic guar, cationic cassia, cationic starch and the like and mixtures thereof;
Oils and hydrocarbons including but not limited to petroleum-derived oils (such as mineral oil), isohexadecane, isododecane, synthetic oils, natural and synthetic oils and derivatives thereof, of avocado oil, coconut oil, olive oil, safflower oil, grape seed oil, castor oil, palm kernel oil, lanolin and the like and mixtures thereof;
Fatty esters, including but not limited to. isopropyl myristate, isopropyl palmitate, diisopropyl adipate, isocetyl stearate, cetyl esters, ethylhexyl palmitate, isostearyl neopentanoate, C12-15 alcohol benzoate, and the like and mixtures thereof;
Organically substituted silicone polymers including, but not limited to, alkyl functional siloxanes, glycol functional siloxanes, phenyl functional siloxanes, vinyl silicones, dimethicone crosspolymers, dimethicone/vinyl dimethicone crosspolymers, dimethicone/phenyl vinyl dimethicone crosspolymers, vinyl dimethicone/lauryl dimethicone crosspolymers, lauryl polydimethylsiloxyethyl dimethicone/bis-vinyl dimethicone crosspolymer, alkyl silicones, stearoxytrimethylsilane, ethylene-dimethicone copolymer, polyethylsiloxanes, alkyl silicones including caprylyl methicone, lauryl methicone and stearoxymethicone and the like and mixtures thereof.

Additional additives may be added to these formulations to provide other hair care benefits without effecting the performance of the invention. Such additives may include:
Hair shine ingredients, including but not limited to, phenyltrimethicone, diphenylsiloxy phenyl trimethicone, diphenyl dimethicone, caprylic/capric triglycerides, mineral or natural oils, alkyl benzoates and the like. When oils or triglycerides are used in the present composition, their concentration is very preferably maintained low enough (e.g., less than about 10% or less than about 5% or less than about 2% or less than about 1.5%) to add shine to the hair without rendering the hair greasy or wet;
Humectants, including glycerin, hyaluronic acid and its salts, propylene glycol, butylene glycol and the like and mixtures thereof;
Sunscreen ingredients such as, without limitation, one or more of titanium dioxide, zinc oxide, and organic sunscreens to protect the hair from sun bleaching, discoloration or fading; such as for color-treated hair and to preserve hair color;
Formulation aesthetic modifiers may include thickener components, fragrance components, pH adjustment components, plasticizer components, appearance modifiers or anti-oxidant components. Such aesthetic modifier components may help to make delivery of the functional ingredients more acceptable by, for example, helping the active ingredients spread, diluting the active ingredients, stabilizing the active ingredients, and/or improving the look and feel of the composition when applied to the hair.
Other components effective in making the composition appealing to the consumer, such as (without limitation) essential oils, botanicals, scents, nucleic acids, specialty extracts, proteins, amino acids, algae derivatives, amino acids, and vitamins and the like.

Example 7

A set of nonionic emulsions are prepared according to the general method set forth above, by inversion of a water-in-oil emulsion to an oil-in-water emulsion.

TABLE 8

Non-Ionic Emulsion Conditioners

| | Formulation | | | |
|---|---|---|---|---|
| Ingredient | 19 | 20 | 21 | 22 |
| PHASE A (silicone phase) | | | | |
| Cyclopentasiloxane | 10.00 | | | |
| Dimethicone (5 cSt) | | 15.00 | 10.00 | 15.00 |

TABLE 8-continued

Non-Ionic Emulsion Conditioners

| Ingredient | Formulation 19 | 20 | 21 | 22 |
|---|---|---|---|---|
| Propoxytetramethyl Piperidinyl Dimethicone (90,000 cSt) | 5.00 | 5.00 | 7.50 | 5.00 |
| Cyclomethicone and trimethylsiloxysilicate | 10.00 | | | |
| Dimethicone and trimethylsiloxysilicate | | 10.00 | | 10.00 |
| Cetearyl Alcohol | 2.00 | 2.00 | 2.00 | 2.00 |
| Laureth-4 | 2.00 | 2.00 | 2.00 | 2.00 |
| Laureth-23 | 2.00 | 2.00 | 2.00 | 2.00 |
| Hydroxyethyl Acrylate/Sodium Acryloyldimethyl Taurate Copolymer | 0.35 | 0.35 | 0.35 | 0.35 |
| PHASE B | | | | |
| DI Water | 68.65 | 63.65 | 76.15 | 63.65 |

Hair treated, then combed with one of Formulations 19 through 12 shows at least 70% frizz reduction relative to untreated tresses.

TABLE 9

Leave-In Nonionic Oil-In-Water Emulsion Sprayable Conditioners

| Ingredient | Formulations 23 | 24 | 25 | 26 |
|---|---|---|---|---|
| PHASE A | | | | |
| Cyclopentasiloxane | 10.00 | | | |
| Dimethicone (5 cSt) | | 15.00 | 10.00 | 15.00 |
| Propoxytetramethyl Piperidinyl Dimethicone (90,000 cSt) | 5.00 | 5.00 | 7.50 | 5.00 |
| Cyclomethicone and trimethylsiloxysilicate (100 cps) | 10.00 | | | |
| Dimethicone and trimethylsiloxysilicate (500 cps) | | 10.00 | | 10.00 |
| Cetearyl Alcohol | 1.00 | 1.00 | 1.00 | 1.00 |
| Laureth-4 | 2.50 | 2.50 | 2.50 | 2.50 |
| Laureth-23 | 2.50 | 2.50 | 2.50 | 2.50 |
| PHASE B | | | | |
| DI Water | 69.00 | 64.00 | 76.00 | 64.00 |

Hair treated, then combed with one of Formulations 23 through 26 shows at least 70% frizz reduction relative to untreated tresses.

Water-in-Oil Emulsions Anti-Frizz Leave in Conditioners/Combing Cremes

Water-in-oil leave-in conditioners have an advantage over oil-in-water emulsions conditioners in that they deposit the hydrophobic combing and anti-fizz components more directly and completely onto the surface of the hair, which results in a more uniform film of these ingredients on the hair.

Generally speaking, nonionic water-in-oil emulsions contain water, a nonionic silicone emulsifier, and a silicone phase. The nonionic water-in-oil emulsions are formed as follows:

1) Phase A: Add the hydrophobic ingredients to a suitable container which is large enough to allow the addition of the water phase. Heat to a temperature slightly greater than the melting point of the ingredient having the highest melting point. Mix until uniform.

2) Phase B: In a separate container, mix together the water and hydrophilic ingredients until uniform.

3) Slowly add Phase B to Phase A using homogenization to drive down the droplet size of the water to 1 μm or less and mix until uniform.

Example 7

Table 10 shows exemplary formulations for a non-ionic water-in-oil leave-in conditioner.

TABLE 10

| Ingredients | Formulations 35 | 36 | 37 | 38 | 39 | 40 |
|---|---|---|---|---|---|---|
| Phase A | | | | | | |
| Cyclopentasiloxane (and) PEG/PPG-18/18 Dimethicone | 10.00 | | 10.00 | | 10.00 | |
| Dimethicone (and) PEG/PPG-18/18 Dimethicone | | 10.00 | | 10.00 | | 10.00 |
| Cyclopentasiloxane | 10.00 | 10.00 | 6.00 | 10.00 | 5.00 | 10.00 |
| Propoxytetramethyl Piperidinyl Dimethicone (90,000 cSt) | 5.00 | 5.00 | 7.50 | 6.50 | 3.50 | 2.50 |
| Cyclopentasiloxane (and) Dimethiconol (~5000 cps) | 5.00 | 5.00 | 4.00 | 5.00 | 5.00 | 7.00 |
| Trimetylsiloxysilicate | 3.00 | 3.00 | | | 5.00 | 5.00 |
| Phase B | | | | | | |
| Water | 65.50 | 65.50 | 71.00 | 67.00 | 70.00 | 64.00 |
| Sodium Chloride | 1.50 | 1.50 | 1.50 | 1.50 | 1.50 | 1.50 |

Hair treated, then combed with one of Formulations 35 through 40 shows at least 70% frizz reduction relative to untreated tresses.

Example 8

The formulations in Table 11 are also for use as non-ionic water-in-oil leave-in conditioners. These formulations are made in a similar manner, however in these water-in-oil emulsions the final homogenization step is not required.

TABLE 11

| Ingredients | Formulations 41 | 42 | 43 |
|---|---|---|---|
| Phase A | | | |
| Dimethicone (and) Dimethicone PEG-10/15 Crosspolymer | 3.00 | 3.50 | 4.00 |
| PEG-10 Dimethicone | 0.50 | 1.00 | 1.50 |
| Cyclopentasiloxane | 10.00 | 10.00 | 15.00 |
| Propoxytetramethyl Piperidinyl Dimethicone | 3.00 | 5.00 | 7.50 |
| Dimethicone 5 cSt | | 5.00 | |
| Cyclopentasiloxane (and) Dimethiconol | | | 2.50 |
| Cyclopentasiloxane (and) Trimetylsiloxysilicate | 6.00 | | |
| Phase B | | | |
| Water | 76.50 | 74.80 | 68.00 |
| Sodium Chloride | 1.00 | 0.50 | 1.50 |
| Sodium Citrate | | 0.20 | |

Hair treated, then combed with one of Formulations 41 through 43 shows at least 70% frizz reduction relative to untreated tresses.

In view of the present disclosure, those of ordinary skill in the art will appreciate that any of the presently disclosed embodiments of the invention can provide frizz control to hair as a water based hair styling product when such a product is formulated with at least 2.5%, by weight, of a polysiloxane fluid component selected from one or more of:
   i) an amodimethicone component, and
   ii) a polysiloxane component comprising a plurality of hindered amine side chains.

Hair styling products come in multiple formulation types, including gel, creams, lotions, pastes, putties, sprays, mousses and the like. Some of these products may also contain a hair fixative. Hair fixatives are polymers which impart hair holding or style retention properties by "gluing" hair fibers together. Suitable fixative polymers contained in such products may include: polyvinyl pyrrolidone (PVP) and derivatives thereof, polyquaternium polymers and derivatives thereof, acrylate copolymers and derivatives thereof, polyacrylate polymers and derivatives thereof, polyacrylate crosspolymers and derivatives thereof, vinyl alcohol (VP) polymers and derivatives thereof, VP copolymers and derivatives thereof, mixtures containing two or more of these components, and the like.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention. Each and every feature described herein, and each and every combination of two or more of such features, is included within the scope of the present invention provided that the features included in such a combination are not mutually inconsistent. Furthermore, any composition or apparatus of the invention will be understood to comprise, consist essentially of, or consist of one or more element of a claim, and additionally, each and every element not specifically included as an element of a claim shall be considered to have basis herein to be specifically excluded from that claim, in a negative limitation thereof.

Any and all patents, publications, or patent applications cited in this specification are hereby incorporated by reference as part of this specification in its entirety.

I claim:

1. A method of reducing hair fizz, comprising the steps:
   I) applying to hair an emulsion lacking a detersive component comprising
      a) about 2.5% to 5% by weight of propoxytetramethyl piperidinyl dimethicone component,
      b) selected from the group consisting of dimethicone, dimethiconol, phenyl methicone, phenyl methiconol, a phenyl trimethicone, diphenyl dimethicone, phenyl dimethicone, diphenylsiloxy phenyl trimethicone, hexamethylsiloxane, disiloxane, trisiloxane, cyclotetrasiloxane, cyclopentasiloxane and cyclohexasiloxane volatile or non-volatile liquid carrier component; and
      c) water, and
   II) distributing said composition along a plurality of hair shafts; in which, when said emulsion is applied to frizzy hair and permitted to dry according to said method, said hair displays a reduction in hair frizz after incubation at 80° F. and 80% humidity for 6 hours relative to as compared to the amount of hair frizz observed in identical frizzy hair treated with an otherwise identical emulsion in which the propoxytetramethyl piperidinyl dimethicone component is substituted with dimethicone and incubated under identical conditions for an equal time period.

2. A method according to claim 1 wherein said emulsion is selected from a cationic oil-in-water emulsion; a non-ionic oil-in-water emulsion; and a non-ionic water-in-oil emulsion.

3. A method according to claim 1 wherein said emulsion comprises one or more fatty quaternary ammonium salt, fatty amine, fatty alcohol or fatty alcohol derivative thereof.

4. A method according to claim 3 wherein said fatty alcohol or non-ionic derivative is esterification product of a fatty alcohol and a polyethylene glycol.

5. A method according to claim 1 wherein said emulsion comprises one or more water-soluble thickener.

6. A method according to claim 5 wherein said one or more water-soluble thickener is selected from the group consisting of cellulose-based thickeners, guar gums, cassia gums, locust bean gums, xanthan gums, acacia senegal gums, caesalpina spinosa gums, a clay, acrylamidopropyltrimonium chloride/acrylates copolymers, derivatized and underivatized carbomers, an organically modified clay, and mixtures thereof.

7. A method according to claim 2 wherein said emulsion is a cationic oil-in-water emulsion and comprises one or more fatty quaternary ammonium salts.

8. A method according to claim 2 wherein said emulsion is selected from a non-ionic oil-in-water emulsion; and a non-ionic water-in-oil emulsion and comprises one or more nonionic emulsifiers.

9. A method according to claim 1 wherein the emulsion further comprises one or more components selected from the group consisting of a colorant component, a detangling aid, a hair shine ingredient, a humectant, a sunscreen ingredient, an aesthetic modifier component, a thickener component, a preservative component, a fragrance component, a pH adjustment component, a plasticizer component, an appearance modifier, an antioxidant component, an essential oil component, a botanical component, a scent component, a nucleic acid component, a protein, an amino acid and a vitamin.

* * * * *